United States Patent [19]

Demus et al.

[11] Patent Number: 4,486,332
[45] Date of Patent: Dec. 4, 1984

[54] LIQUID CRYSTALLINE NEMATIC SUBSTANCES

[75] Inventors: Dietrich Demus; Horst Zaschke, both of Halle; Hans-Matthias Vorbrodt, Quedlinburg; Sylvia Deresh, Barleben, all of German Democratic Rep.

[73] Assignee: VEB Werk für Fernsehelektronik im VEB Kombinat Mikroelektronik, Berlin-Oberschoeneweide, German Democratic Rep.

[21] Appl. No.: 405,214

[22] Filed: Aug. 4, 1982

[30] Foreign Application Priority Data

Aug. 18, 1981 [DD] German Democratic Rep. ... 232636

[51] Int. Cl.³ .................. G02F 1/13; C09K 3/34; C07D 319/06; C07D 319/04
[52] U.S. Cl. .................. 252/299.61; 252/299.5; 252/299.63; 350/350 R; 350/350 S; 549/369; 549/373; 549/374; 549/375
[58] Field of Search .............. 260/340.7; 350/350 R, 350/350 S; 252/299.5, 299.61, 299.63; 549/369, 373, 374, 375

[56] References Cited

U.S. PATENT DOCUMENTS

| | | | |
|---|---|---|---|
| 2,307,894 | 1/1943 | Mikeska | 260/340.7 |
| 4,273,929 | 6/1981 | Boller et al. | 252/299.61 |
| 4,298,528 | 11/1981 | Sethofer | 252/299.61 |
| 4,322,354 | 3/1982 | Sorkin | 252/299.61 |
| 4,323,473 | 4/1982 | Sethofer | 252/299.61 |
| 4,323,504 | 4/1982 | Sethofer | 252/299.61 |
| 4,325,830 | 4/1982 | Sethofer | 252/299.61 |
| 4,344,856 | 8/1982 | Demus et al. | 252/299.61 |
| 4,348,324 | 9/1982 | Demus et al. | 252/299.61 |
| 4,356,104 | 10/1982 | Hsu | 252/299.61 |

FOREIGN PATENT DOCUMENTS

| | | | |
|---|---|---|---|
| 56501 | 7/1982 | European Pat. Off. | 252/299.61 |
| 139852 | 1/1980 | German Democratic Rep. | 252/299.61 |
| 139867 | 1/1980 | German Democratic Rep. | 252/299.61 |
| 56-164179 | 12/1981 | Japan | 252/299.61 |
| 2067586 | 7/1981 | United Kingdom | 252/299.61 |

OTHER PUBLICATIONS

Gary, G. W. et al., Mol. Cryst. Liq. Cryst., vol. 53, pp. 147–166, (1979).
Osman, M. M., et al., Mol. Cryst. Liq. Cryst., vol. 56, (Letters), pp. 105–109, (1979).

*Primary Examiner*—Teddy S. Gron
*Attorney, Agent, or Firm*—Jordan and Hamburg

[57] ABSTRACT

The invention relates to liquid crystal nematic substances based on new derivatives of 1,3-dioxanes in electro-optical components, which are used, for instance, as displays in electronic clocks and computer systems.

The subject of the invention is nematic liquid crystal substances with favorable properties concerning melting and clear temperatures, stability against thermal stress and electrical fields, low viscosity and low threshold voltage.

It was found that liquid crystal 2,5-di-substituted cyclohexyl derivatives of 1,3 dioxanes, having the general formula

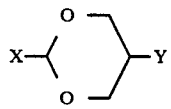

wherein X = 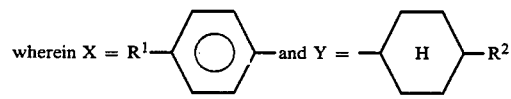

or X = 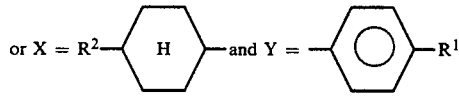

or X = $R^2$ and Y = 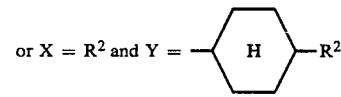

or X = 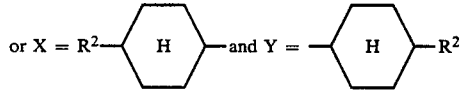

or X = 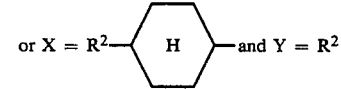 and Y = $R^2$ $R^1 = C_nH_{2n+1}$; $C_nH_{2n+1}O$; $C_nH_{2n+1}COO$; CN; NO₂; F; Cl; Br
and $R^2 = C_nH_{2n+1}$ with n+1 to 9
are suitable for use in electro-optical components.

12 Claims, No Drawings

LIQUID CRYSTALLINE NEMATIC SUBSTANCES

BACKGROUND OF THE INVENTION AND PRIOR ART STATEMENT

This invention relates to liquid crystal nematic substances based on new derivatives of 1,3-dioxanes for use in electrooptical components, which can modulate incident or transmitted light as well as exhibit numbers, symbols and images. Electrooptical components of this kind can, for instance, be used as displays in electronic clocks, computer systems and instruments.

The literature discloses a large number of liquid crystal compounds, which are sometimes suggested for use in electro-optical displays: D. Demus, H. Demus and H. Zaschke: Flüssige Kristalle in Tabellen, VEB Deutscher Verlag für Grundstoffindustrie, Leipzig 1974—D. Demus in: "Non-emissive Electrooptic Displays" edited by R. A. Kmetz and F. K. von Willisen Plenum Press New York—London 1976 pp. 83-117—V. V. Titov: Proceedings 3$^{rd}$ Liquid Crystal Conference of Socialistic Countries, Budapest 1979—G. Weber, P. del Pino, L. Pohl: Proceedings 10. Freiburger Arbeitstagung Flüssigkristalle 1980.

No pure compound is known which exhibits all the required properties for use in displays. Therefore, mixtures of several liquid crystal substances are always used. The requirements placed on the mixtures (melting- and clearing point, operating temperature range, threshold voltage, time behavior, temperature dependency of the properties) are increasingly severe, and additionally, new mixtures are required for new areas of use. There is therefore a continuing search for new liquid crystal mixtures to meet these demands.

Derivatives of 1,3-dioxane having the general formula

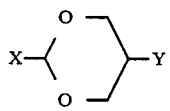

wherein

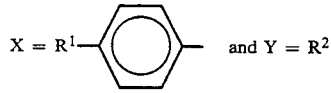

or

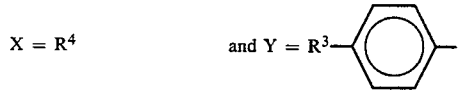

or

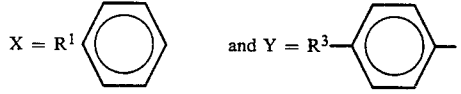

are known for use in electro-optical components (DD-WP 139 867). A large number of such compounds with two six-membered rings are only monotropic liquid crystals, while the compounds with three six-membered rings have comparatively low solubility.

SUMMARY OF THE INVENTION

The object of the invention is to provide nematic liquid crystal substances having desirable melting and clear temperatures, stability against thermal stress and electrical fields, low viscosity and low threshold voltage.

In accordance with the invention it has been discovered that liquid crystal 2,5 di-substituted cyclohexyl derivatives of 1,3-dioxanes having the general formula

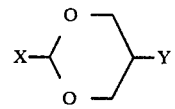

wherein

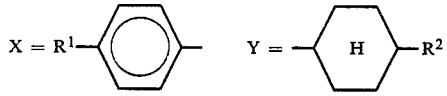

or

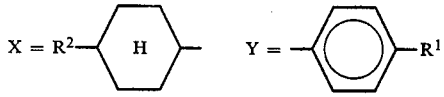

or

or

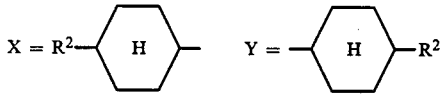

or

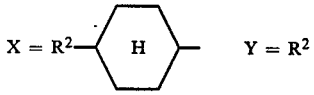

with $R^1 = C_nH_{2n+1}$; $C_nH_{2n+1}O$; $C_nH_{2n+1}COO$; $NO_2$; F; Cl; Br; CN, $R^2 = C_nH_{2n+1}$ and $n = 1$ to 9; are useful in electro-optical components.

DETAILED DESCRIPTION OF PREFERRED EMBODIMENTS

The 2,5-di-substituted cyclohexyl derivatives of 1,3-dioxanes are liquid crystals over a range of conditions, with often high clearing points (Table 1-3). They are stable to heat, visible and ultra-violet radiation and electrical D.C. and A.C. fields. In comparison to the analogous phenyl derivatives of 1,3-dioxane, they have low viscosity, which means low switching times in electro-optical components; this is particularly advantageous. The substances are used to advantage in mixtures with each other, as well as in mixtures with the 1,3-dioxanes mentioned in DD-WP 139 852 (1978), or other liquid crystal and non-liquid crystal substances.

These compounds can be prepared by known methods as described by: (H. Zaschke, H. M. Vorbrodt, D. Demus, W. Weissflog: DD-WP 139 852 (1978); H. M. Vorbrodt, S. Deresch, H. Kresse, A. Wiegeleben, D. Demus, H. Zaschke: J. prakt. Chem.im Druck)—alkanals, diols. Thus an aldehyde reacts as follows with a 1,3-diol in the presence of an acid catalyst:

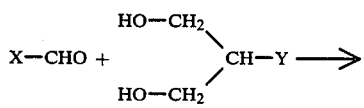

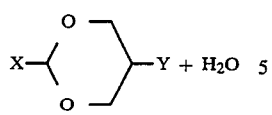

The required aldehydes of the cyclohexane series were produced as follows:

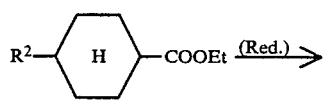

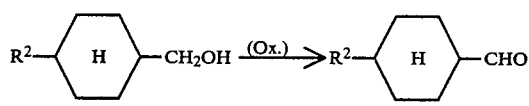

The the 2-(4-substituted cyclohexyl)-propane-1,3-diol is prepared as follows:

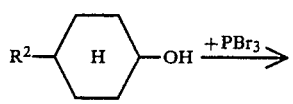

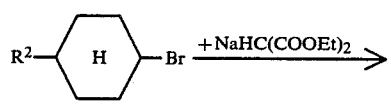

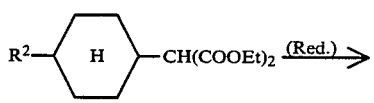

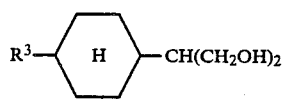

In this way, cyclohexanols which are largely or entirely of the cis-configuration give good yields of 2-(4-substituted-cyclohexyl)-propane-1,3-diols enriched in the trans form.

EXAMPLES
EXAMPLE 1

Substances to be used according to the invention are listed in Tables 1 to 3. The letters used in the tables mean the following: K=crystalline solid; S=smectic phase; N=nematic phase; I=isotropic liquid,

TABLE 1

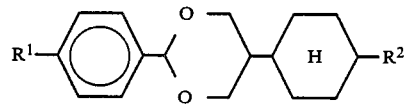

| Comp. | $R^1$ | $R^2$ | K | | S | | N | | I |
|---|---|---|---|---|---|---|---|---|---|
| 1a | CN | $C_2H_5$ | . | 118 | — | | . | 206 | . |
| 1b | CN | $C_5H_{11}$ | . | 84 | — | | . | 220 | . |
| 1c | CN | $C_6H_{13}$ | . | 95 | — | | . | 214 | . |
| 1d | $NO_2$ | $C_6H_{13}$ | . | 93 | . | 123 | . | 193 | . |
| 1e | $C_6H_{13}$ | $C_2H_5$ | . | | . | 162 | — | | . |
| 1f | $C_2H_5O$ | $C_2H_5$ | . | 96 | . | 166 | . | 184 | . |
| 1g | $C_5H_{11}O$ | $C_2H_5$ | . | | . | | . | 172 | . 173 . |
| 1h | $C_5H_{11}O$ | $C_6H_{13}$ | . | | . | 45 | . | 203 | — . |

TABLE 2

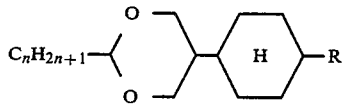

| Comp. | n | R | K | | $S_B$ | | I |
|---|---|---|---|---|---|---|---|
| 2a | 6 | $C_6H_{13}$ | . | 34.7 | . | 109 | . |
| 2b | 6 | $C_2H_5$ | . | <25 | . | 89 | . |

TABLE 3

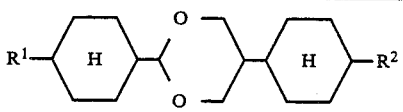

| Comp | $R^1$ | $R^2$ | K | | S | | I |
|---|---|---|---|---|---|---|---|
| 3a | $C_6H_{13}$ | $C_6H_{13}$ | . | 55 | . | 229 | . |
| 3b | $C_6H_{13}$ | $C_2H_5$ | . | <25 | . | 194 | . |

EXAMPLE 2

The substances according to the invention, are used to advantage in electro-optical cells made as described below. The liquid crystal layer is located between two glass plates with internally opened transparent electrodes (preferably comprising $SnO_2$), which by means of clamps are maintained at a fixed distance of 5–30 μm. By preliminary treatment (slope evaporation or rubbing in a defined direction), the electrodes are first made definitely anisotropic and twisted against each other at a preferred direction of 90°. If the device is located between crossed polarizers, it will transmit light. In an electrical field above the threshold voltage $U_o$, the cell is impervious to light. This cell, which is a rotating cell according to Schadt/Helfrich, is filled with the following mixture of substances of positive dielectric anisotropy:

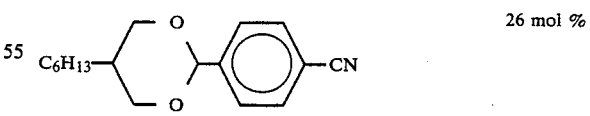

26 mol %

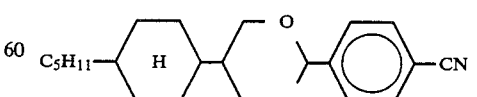

14 mol %

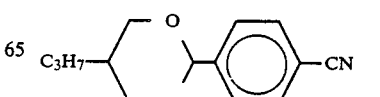

60 mol %

Properties of the mixture at a temperature of 20° C.:
  Threshold voltage $U_o$=0.8 V/500 Hz.
  Layer thickness d=15.5 μm.
  Switching times at U=1.6 V.
  $t_{E50\%}$=1490 ms.
  $t_{A50\%}$=170 ms.
Transformation temperatures of the nematic eutectic mixture:
  Melting: 18°–19° C.; clear: 73°–76° C.
The mixture can be strongly supercooled: When stored at a temperature of −20° C., the mixture does not crystallize for approximately 2 hours.

EXAMPLE 3

The substances of this invention have surprisingly low melting enthalpies:
  Compound 1f:$H_S$=17.5 kJ/mol;
  2a:$H_S$=26.0 kJ/mol.
Low melting enthalpies cause especially strong depression of the melting points of mixtures, which is of importance for use at low temperatures.

We claim:

1. A liquid crystal nematic composition, comprising at least one 2,5-di-substituted cyclohexyl derivative of 1,3-dioxane having the general formula:

X—[dioxane]—Y, wherein X = R¹—[phenyl]— and Y = —[cyclohexyl]—R² or X = R²—[cyclohexyl]— and Y = —[cyclohexyl]—R² wherein:
  $R^1 = C_nH_{2n+1}$; $C_nH_{2n+1}O$; $C_nH_{2n+1}COO$; CN; $NO_2$; F; Cl; Br
  $R_2 = C_nH_{2n+1}$ and n=1 to 9 and mixtures of said derivatives.

2. A liquid crystal nematic composition according to claim 1, comprising a compound which is NC—[phenyl]—[dioxane]—[cyclohexyl]—$C_2H_5$.

3. A liquid crystal nematic composition according to claim 1, comprising a compound which is NC—[phenyl]—[dioxane]—[cyclohexyl]—$C_5H_{11}$.

4. A liquid crystal nematic composition according to claim 1, comprising a compound which is NC—[phenyl]—[dioxane]—[cyclohexyl]—$C_6H_{13}$.

5. A liquid crystal nematic composition according to claim 1, comprising a compound which is $O_2N$—[phenyl]—[dioxane]—[cyclohexyl]—$C_6H_{13}$.

6. A liquid crystal nematic composition according to claim 1, comprising a compound which is $C_6H_{13}$—[phenyl]—[dioxane]—[cyclohexyl]—$C_2H_5$.

7. A liquid crystal nematic composition according to claim 1, comprising a compound which is $C_2H_5O$—[phenyl]—[dioxane]—[cyclohexyl]—$C_2H_5$.

8. A liquid crystal nematic composition according to claim 1, comprising a compound which is $C_5H_{11}O$—[phenyl]—[dioxane]—[cyclohexyl]—$C_2H_5$.

9. A liquid crystal nematic composition according to claim 1, comprising a compound which is $C_5H_{11}O$—[phenyl]—[dioxane]—[cyclohexyl]—$C_6H_{13}$.

10. A liquid crystal nematic composition according to claim 1, comprising a compound which is $C_6H_{13}$—[cyclohexyl]—[dioxane]—[cyclohexyl]—$C_6H_{13}$.

11. A liquid crystal nematic composition according to claim 1, comprising a compound which is $C_6H_{13}$—[cyclohexyl]—[dioxane]—[cyclohexyl]—$C_2H_5$.

12. An electro-optical device for modulation of incident and transmitted light, and for the display of numerals, symbols, or images, containing at least one nematic liquid crystal composition according to claim 1.

* * * * *